United States Patent
Guo et al.

(10) Patent No.: US 12,274,468 B1
(45) Date of Patent: Apr. 15, 2025

(54) STEP CUTTING THROMBECTOMY DEVICE AND THROMBECTOMY SYSTEM

(71) Applicant: SUZHOU ZENITH VASCULAR SCITECH LIMITED, SIP Suzhou (CN)

(72) Inventors: Liyou Guo, SIP Suzhou (CN); Shuang Li, SIP Suzhou (CN); Jie Xia, SIP Suzhou (CN)

(73) Assignee: SUZHOU ZENITH VASCULAR SCITECH LIMITED (CN)

( * ) Notice: Subject to any disclaimer, the term of this patent is extended or adjusted under 35 U.S.C. 154(b) by 0 days.

(21) Appl. No.: 18/855,297

(22) PCT Filed: Nov. 30, 2022

(86) PCT No.: PCT/CN2022/135226
§ 371 (c)(1),
(2) Date: Oct. 8, 2024

(87) PCT Pub. No.: WO2024/011820
PCT Pub. Date: Jan. 18, 2024

(30) Foreign Application Priority Data

Jul. 13, 2022 (CN) .......................... 202210817852.4

(51) Int. Cl.
*A61B 17/221* (2006.01)
*A61B 17/00* (2006.01)
(Continued)

(52) U.S. Cl.
CPC .............. *A61B 17/320758* (2013.01); *A61B 17/00234* (2013.01); *A61B 17/22* (2013.01);
(Continued)

(58) Field of Classification Search
CPC ............ A61B 17/221; A61B 17/22032; A61B 17/320758; A61B 17/320725;
(Continued)

(56) References Cited

U.S. PATENT DOCUMENTS 5,108,419 A * 4/1992 Reger ................... A61F 2/0105
606/159
9,364,255 B2 * 6/2016 Weber ............ A61B 17/320725
(Continued)

FOREIGN PATENT DOCUMENTS

| CN | 102056557 A | 5/2011 |
| CN | 102316809 A | 1/2012 |

(Continued)

OTHER PUBLICATIONS

International Search Report and Written Opinion with English Translation for PCT Application No. PCT/CN2022/135226, dated Apr. 7, 2023, 11 pages.

(Continued)

*Primary Examiner* — Tuan V Nguyen
(74) *Attorney, Agent, or Firm* — Dickinson Wright PLLC

(57) ABSTRACT

A step-cutting thrombectomy device and a thrombectomy system is disclosed. The step-cutting thrombectomy device includes the following: multiple first cutting components capable of elastically expanding in a radial direction and configured to cut a thrombus in a longitudinal direction of a blood vessel; multiple second cutting components, capable of elastically expanding in the radial direction and configured to cut the thrombus in a circumferential direction of the blood vessel a collection device, configured to collect a crushed thrombus; and a push tube. The first cutting components, the second cutting components and the collection device are sequentially disposed on the push tube from the proximal end to the distal end.

20 Claims, 11 Drawing Sheets

(51) Int. Cl.
 *A61B 17/22* (2006.01)
 *A61B 17/3207* (2006.01)
(52) U.S. Cl.
 CPC .............. *A61B 17/320725* (2013.01); *A61B 2017/00238* (2013.01); *A61B 2017/00477* (2013.01); *A61B 2017/00561* (2013.01); *A61B 2017/00778* (2013.01); *A61B 2017/22079* (2013.01); *A61B 2017/320716* (2013.01); *A61B 2217/005* (2013.01)
(58) Field of Classification Search
 CPC .. A61B 17/00234; A61B 2017/320733; A61B 2017/00238
 See application file for complete search history.

(56) References Cited

U.S. PATENT DOCUMENTS

| | | | |
|---|---|---|---|
| 2006/0287667 A1* | 12/2006 | Abela | ............ A61B 17/320758 606/200 |
| 2021/0402157 A1 | 12/2021 | Keating et al. | |
| 2022/0015784 A1 | 1/2022 | Erlick et al. | |

FOREIGN PATENT DOCUMENTS

| | | | |
|---|---|---|---|
| CN | 208851573 | U | 5/2019 |
| CN | 111227908 | A | 6/2020 |
| CN | 212547088 | U | 2/2021 |
| CN | 113425373 | A | 9/2021 |
| CN | 215018482 | U | 12/2021 |
| CN | 215606575 | U | 1/2022 |
| CN | 114209392 | A | 3/2022 |
| CN | 114886505 | A | 8/2022 |

OTHER PUBLICATIONS

First Office Action with English Translation for Chinese Application No. 202210817852.4, dated Aug. 22, 2022, 14 pages.
Notice of Grant with English Translation for Chinese Application No. 202210817852.4, dated Aug. 31, 2022, 3 pages.

* cited by examiner

STEP CUTTING THROMBECTOMY DEVICE AND THROMBECTOMY SYSTEM

CROSS-REFERENCE TO RELATED APPLICATIONS

This is a National Stage Application, filed under 35 U.S.C. 371, of International Patent Application No. PCT/CN2022/135226, filed on Nov. 30, 2022, which claims priority to Chinese patent application No. 202210817852.4 filed with China National Intellectual Property Administration (CNIPA) on Jul. 13, 2022, the disclosures of which are incorporated herein by reference in their entireties.

This application claims the priority of Chinese patent application No. 202210817852.4 filed Jul. 13, 2022, the disclosure of which is incorporated herein by reference in its entirety.

TECHNICAL FIELD

The present application relates to the field of medical devices and, for example, to a step-cutting thrombectomy device and a thrombectomy system.

BACKGROUND

Pulmonary embolism (PE) is a potentially life-threatening disease. Acute PE causes systemic hypotension and even total heart failure, thereby resulting in the death of a patient. PE is one of the three major fatality cardiovascular diseases along with myocardial infarctions and stroke. A thrombus is the most common embolus in the pulmonary embolism. The main treatment methods in the related art are pulmonary endarterectomy, thrombus aspiration, catheter thrombolysis, mechanical thrombectomy, and other therapeutic surgeries. The mechanical thrombectomy mainly removes a thrombus by crushing, aspiration, a stentriever or a net basket and has become a hot spot of research in recent years.

For the stentriever in the related art, the stent is generally embedded into a thrombus to crush the thrombus, and the crushed thrombus is removed from the body under aspiration. However, if the mesh of the stent is too sparse, the thrombus will not be fully cut; and if the mesh of the stent is too dense, the cutting force to the thrombus becomes insufficient, the stent fails to be fully embedded into the thrombus, and the thrombus adhering to the blood vessel wall cannot be removed completely.

SUMMARY

The present application provides a step-cutting thrombectomy device and a thrombectomy system which can fully cut a thrombus on the vessel wall and completely remove the crushed thrombus.

An embodiment of the present application provides a step-cutting thrombectomy device. The step-cutting thrombectomy device includes multiple first cutting components capable of elastically expanding in the radial direction and configured to cut a thrombus in the longitudinal direction of a blood vessel; multiple second cutting components capable of elastically expanding in the radial direction and configured to cut a thrombus in the circumferential direction of the blood vessel; a collection device, configured to trap and collect the crushed thrombus; and a push tube. The multiple first cutting components, the multiple second cutting components and the collection device are sequentially disposed on the push tube from the proximal end to the distal end.

The thrombectomy system includes an aspiration pump, a hemostasis valve, a luer hub, an aspiration catheter, an outer tube and the aforementioned step-cutting thrombectomy device.

Figure 1:
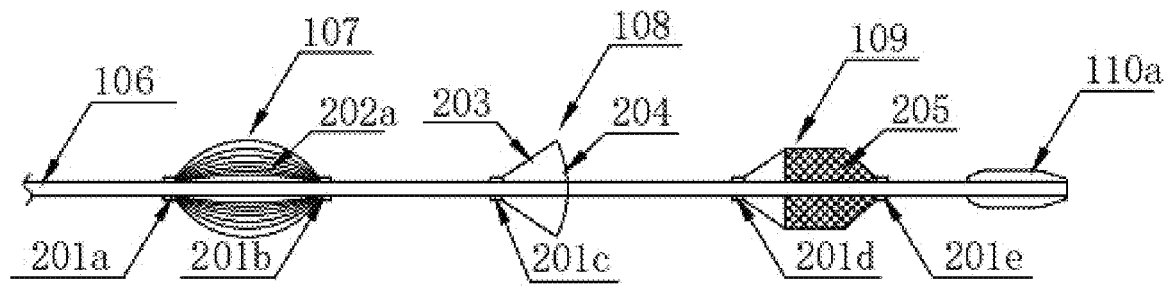
FIG. 1 is a schematic view of a step-cutting thrombectomy device which is released according to an embodiment of the present application.

REFERENCE LIST 101 aspiration pump
102a first hemostasis valve 103a first luer hub
102b second hemostasis valve
103b second luer hub
104 aspiration catheter
105 outer tube
106 push tube
107 first cutting component
108 second cutting component
109 collection device
110a first tip guide cap
110b second tip guide cap
201a proximal first connecting ring
201aa proximal second connecting ring
201c proximal third connecting ring
201d proximal fourth connecting ring
201dd proximal fifth connecting ring
201b distal first connecting ring
201e distal second connecting ring
202a first longitudinal cutting member
202b second longitudinal cutting member
203 first connecting rod
204 transverse cutting ring
204a first cutting ring
204aa third cutting ring
204b second cutting ring
204bb fourth cutting ring
205 first filter mesh;
206 second connecting rod
207 third connecting rod
208 second filter mesh
901 first cutting half-ring
902 second cutting half-ring
1003 connecting tube
1601 skeleton
1701 inner tube
1801 guidewire
1802 thrombus
1803 blood vessel
2101 embolus

DETAILED DESCRIPTION

In the description of the present application, it is to be noted that orientations or position relations indicated by terms such as "upper", "lower", "left", "right", "vertical", "horizontal", "in", and "out" are based on the drawings or those of the product of the present application usually placed during use. These orientations or position relations are intended only to facilitate and simplify the description of the present application and not to indicate or imply that a device or element referred to must have such particular orientations or must be configured or operated in such particular orientations. Thus, these orientations or position relations are not to be construed as limiting the present application. Moreover, the terms "first", "second", "third" and the like are used only for distinguishing between descriptions and are not to be construed as indicating or implying relative importance. In the description of the present application, unless otherwise noted, the term "a plurality of" or "multiple" means two or more.

In the description of the present application, it is to be noted that unless otherwise expressly specified and limited, the term "configured" or "connected" is to be construed in a broad sense, for example, as fixedly connected, detachably connected or internally connected; or mechanically connected or electrically connected. For those of ordinary skill in the art, specific meanings of the preceding terms in the present application may be construed according to specific situations.

In the present application, unless otherwise expressly specified and limited, when a first feature is described as "on" or "below" a second feature, the first feature and the second feature may be in direct contact or be in contact via another feature between the two features instead of being in direct contact. Moreover, when the first feature is described as "on", "above" or "over" the second feature, the first feature is right on, above or over the second feature, the first feature is obliquely on, above or over the second feature, or the first feature is simply at a higher level than the second feature. When the first feature is described as "under", "below" or "underneath" the second feature, the first feature is right under, below or underneath the second feature, the first feature is obliquely under, below or underneath the second feature, or the first feature is simply at a lower level than the second feature.

Embodiments of the present application are described in detail below. Examples of the embodiments are illustrated in the drawings, where the same or similar reference numerals indicate the same or similar elements or elements having the same or similar functions. The embodiments described below with reference to the drawings are illustrative, are intended to explain the present application, and cannot be construed as limiting the present application. Pulmonary embolism (PE) is a potentially life-threatening disease. Acute PE causes systemic hypotension and even total heart failure, thereby resulting in the death of a patient. PE is one of the three major fatality cardiovascular diseases along with myocardial infarctions and stroke. A thrombus is the most common embolus in pulmonary embolism. The main treatment methods in the related art are pulmonary endarterectomy, thrombus aspiration, catheter thrombolysis, mechanical thrombectomy, and other therapeutic surgeries. The mechanical thrombectomy mainly removes a thrombus by crushing, aspiration, stent-retriever thrombectomy or net basket thrombectomy and has become a hot spot of research in recent years. The mechanical thrombectomy is generally performed by expanding a stent, embedding the stent into a thrombus, dragging the thrombus inside an aspiration catheter and aspirating the thrombus out of the body via an aspiration device. However, if the mesh of the stent is too sparse, the thrombus will not be fully cut; if the mesh of the stent is too dense, the cutting force to the thrombus becomes insufficient, the stent fails to be fully embedded into the thrombus, and the thrombus adhering to the vessel wall cannot be removed completely.

To fully cut a thrombus on the vessel wall and completely remove the crushed thrombus, the embodiments herein provide a step-cutting thrombectomy device and a thrombectomy. The content of the embodiments herein will be described in detail below in connection with FIGS. 1 to 21.

Embodiment One

Figure 17:
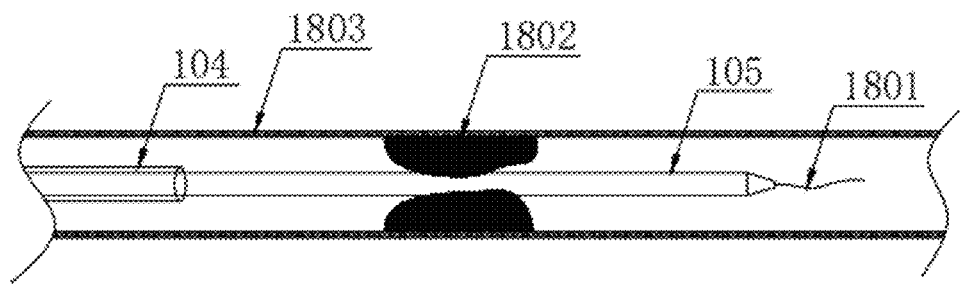
FIG. 17 is a view illustrating a step-cutting thrombectomy device reaching a thrombus according to an embodiment of the present application.

As shown in FIGS. 1 and 17, the step-cutting thrombectomy device includes multiple first cutting components 107 capable of elastically expanding in the radial direction, multiple second cutting components 108 capable of elastically expanding in the radial direction, a collection device 109 and a push tube 106. The multiple first cutting components 107 can cut a thrombus 1802 in the longitudinal direction of a blood vessel 1083. The multiple second cutting components 108 can cut the thrombus 1802 in the circumferential direction of the blood vessel 1803. The collection device 109 is configured to trap and collect the crushed thrombus 1802. The multiple first cutting components 107, the multiple second cutting components 108 and the collection device 109 are sequentially disposed on the outer peripheral wall of the push tube 106 from the proximal end to the distal end.

The terms "the proximal end" and "the distal end" refer to the relative position with respect to the operator of the step-cutting thrombectomy device. The position that is relatively closer to the operator is considered as the proximal end, while the position that is farther away from the operator is considered as the distal end.

In short, with the step-cutting thrombectomy device provided in the embodiment herein, the multiple first cutting components 107, the multiple second cutting components 108 and the collection device 109 are sequentially disposed on the push tube 106 from the proximal end to the distal end of the thrombectomy device, and the first cutting components 107 and the second cutting components 108 are capable of elastically expanding in the radial direction. When the first cutting components 107 and the second cutting components 108 are in a released state, the first cutting components 107 can cut the thrombus 1802 in the longitudinal direction of the blood vessel 1803. In the process of retracting the push tube 106, the second cutting components 108 cut the thrombus 1802 in the circumferential direction of the blood vessel 1803 so that the thrombus 1802 is fully cut. The collection device 109 disposed at the distal end of the thrombectomy device traps and collects the crushed thrombus 1802. The device has the features of simple structure, small loading volume, great adherence and high cutting force to the thrombus 1802 and can fully cut and remove the thrombus 1802 adhering to the wall of the blood vessel 1803 out of the body.

In an embodiment, as shown in FIG. 1, the first cutting component 107 includes a proximal first connecting ring 201a, a distal first connecting ring 201b and at least one first longitudinal cutting member 202a. The proximal end of the first longitudinal cutting member 202a is connected to the proximal first connecting ring 201a, and the distal end of the first longitudinal cutting member 202a is connected to the distal first connecting ring 201b. The proximal first connecting ring 201a is fixedly sleeved on the push tube 106. The distal first connecting ring 201b is slidably disposed on the push tube 106.

When being released from an outer tube 105, the first longitudinal cutting member 202a gradually expands towards the wall of the blood vessel as the temperature rises and cuts the thrombus 1802 in the longitudinal direction during the expansion so that the thrombus 1802 is cut into small pieces in the longitudinal direction, thereby helping to remove the thrombus 1802 completely from the wall of the blood vessel.

In an embodiment, the proximal first connecting ring 201a is fixed to the push tube 106 by heat fusion, glue bonding or welding, and the distal first connecting ring 201b is freely connected to the push tube 106 so that the distal first connecting ring 201b can slide back and forth on the outer surface of the push tube 106 in the loading and releasing process of the first cutting component 107.

In some application scenarios, multiple first longitudinal cutting members 202a are provided, and the multiple first longitudinal cutting members 202a are disposed at intervals in a circumferential direction and encircle the push tube 106 from the outside. By circumferentially disposing multiple first longitudinal cutting members 202a, the thrombus 1802 in the blood vessel 1803 can be cut into multiple portions, thereby facilitating the thrombus detachment. In practice, the number of first longitudinal cutting members 202a may be designed according to the size of the thrombus 1802.

Figure 2:
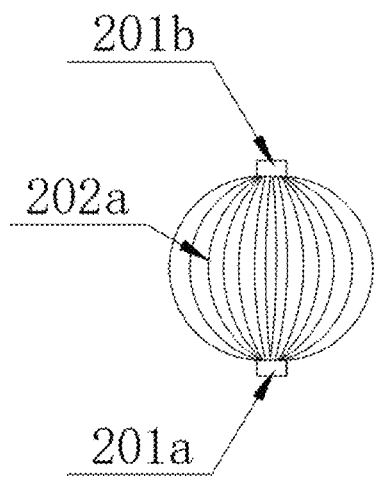
FIG. 2 is a first structure view of a first cutting component according to an embodiment of the present application.
Figure 3:
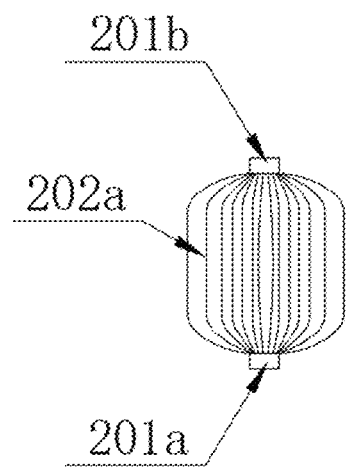
FIG. 3 is a second structure view of a first cutting component according to an embodiment of the present application.

In an embodiment, as shown in FIGS. 2 and 3, the multiple first longitudinal cutting members 202a may encircle to form a spherical or square closed structure.

The first cutting component 107 may be cut from a medical metal tube or woven from medical metal wires. The medical metal material includes medical stainless steel, nickel-titanium memory alloy, cobalt-base alloy, titanium alloy, magnesium alloy, and the like. In other embodiments, the medical metal material may be nickel-titanium memory alloy. The first cutting component 107 has great adherence to the wall and can be adapted to blood vessels 1803 with different diameters and shapes.

In an embodiment, the multiple first cutting components 107 are disposed on the push tube 106 in the longitudinal direction, and the maximum outer diameters of the multiple first cutting components 107 gradually increase from the proximal end to the distal end, thereby ensuring the cutting effect on the thrombus 1802.

Figure 5:
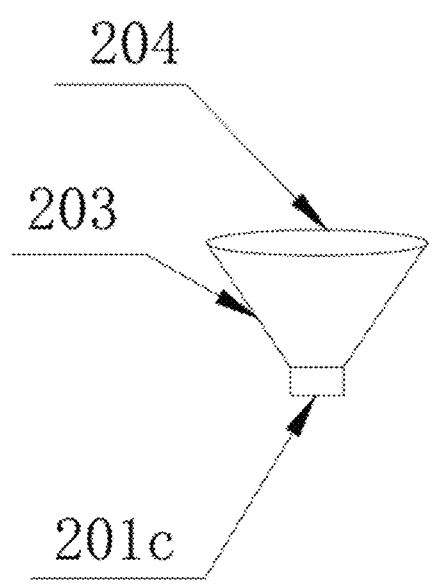
FIG. 5 is a first structure view of a second cutting component according to an embodiment of the present application.

In an embodiment, as shown in FIGS. 1 and 5, the second cutting component 108 includes a proximal third connecting ring 201c, a first connecting rod 203 and a transverse cutting ring 204. At least one transverse cutting ring 204 is provided The transverse cutting ring 204 is distributed in the circumferential direction of the blood vessel 1803, is tightly adhered to the wall of the blood vessel after expansion, and cuts the thrombus 1802 adhering to the wall of the blood vessel during the retraction process. A first end of the first connecting rod 203 is connected to the proximal third connecting ring 201c, and a second end of the first connecting rod 203 is connected to the transverse cutting ring 204. In an embodiment, the second cutting component 108 is horn-shaped.

As shown in FIG. 1, the proximal third connecting ring 201c is fixedly disposed on the push tube 106. In an embodiment, the proximal third connecting ring 201c is fixed to the push tube 106 by heat fusion, glue bonding or welding and is responsible for the release and retraction of the second cutting component 108. The transverse cutting ring 204 is responsible for cutting the thrombus 1802 from the wall of the blood vessel.

Figure 6:
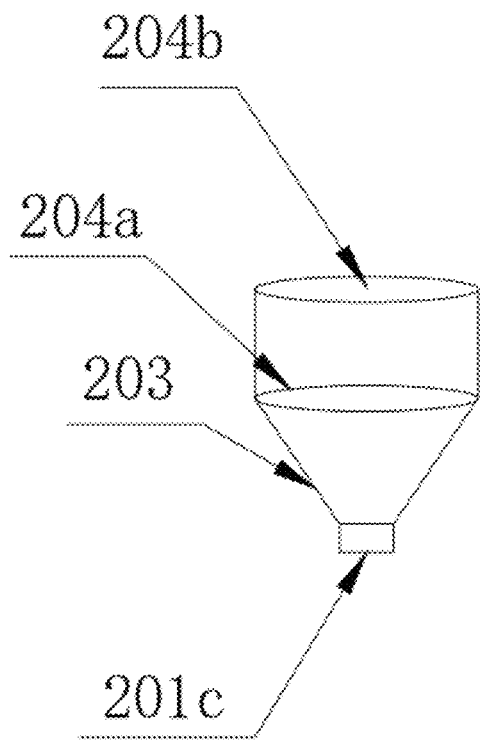
FIG. 6 is a second structure view of a second cutting component according to an embodiment of the present application.

In an embodiment, as shown in FIG. 6, the transverse cutting ring 204 includes a first cutting ring 204a and a second cutting ring 204b. The first cutting ring 204a and the second cutting ring 204b have the same inner diameter and are sequentially disposed on the first connecting rod 203 at intervals in the axial direction of the first connecting rod 203.

Figure 7:
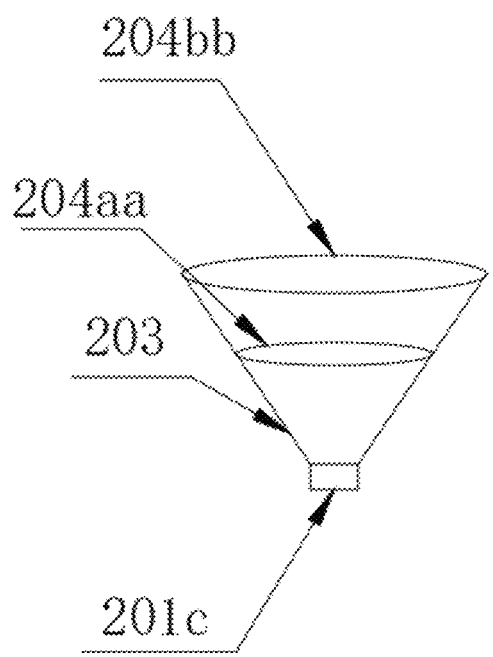
FIG. 7 is a third structure view of a second cutting component according to an embodiment of the present application.

In an embodiment, as shown in FIG. 7, the transverse cutting ring 204 includes a third cutting ring 204aa and a fourth cutting ring 204bb. The inner diameter of the third cutting ring 204aa is less than the inner diameter of the fourth cutting ring 204bb, and the third cutting ring 204aa and the fourth cutting ring 204bb are sequentially disposed on the first connecting rod 203 at intervals in the axial direction of the push tube 106. The fourth cutting ring 204bb having a larger diameter has a stronger support force and can perform secondary cutting on the thrombus 1802, thereby removing the thrombus 1802 more completely. The second cutting component 108 may be cut from medical metal tubing or woven from medical metal wires. The medical metal material includes medical stainless steel, nickel-titanium memory alloy, cobalt-base alloy, titanium alloy and magnesium alloy. In other embodiments, the medical metal material may be nickel-titanium memory alloy. The second cutting component 108 can be adapted to different blood vessels 1803 and has great adherence to the wall and a smaller size.

In an embodiment, the multiple second cutting components 108 are disposed on the push tube 106 in the longitudinal direction, and the maximum outer diameters of the multiple second cutting components 108 gradually increase from the proximal end to the distal end.

Figure 8:
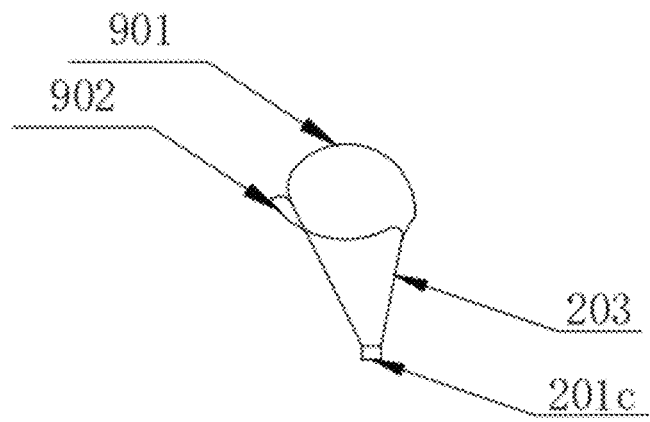
FIG. 8 is a structure view of a transverse cutting ring being a first type of cutting half-ring according to an embodiment of the present application.

In an embodiment, as shown in FIG. 8, the transverse cutting ring 204 includes a first cutting half-ring 901 and a second cutting half-ring 902 that are connected to each other. The two cutting half-rings form a complete circle in the circumferential direction. The transverse cutting ring 204 may be cut from a metal tube, and the connection between the first cutting half-ring 901 and the second cutting half-ring 902 is connected to the first connecting rod 203.

Figure 9:
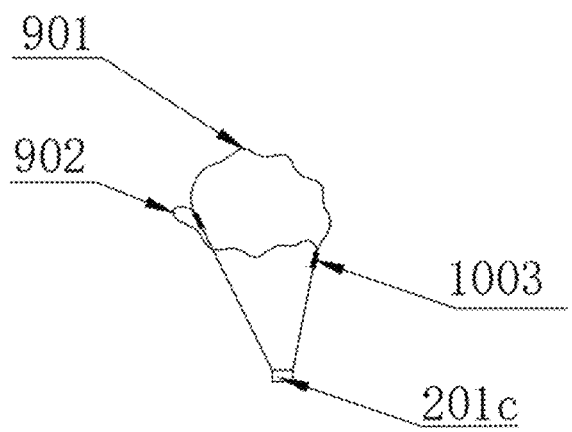
FIG. 9 is a structure view of a transverse cutting ring being a second type of cutting half-ring according to an embodiment of the present application.

In an embodiment, as shown in FIG. 9, the first cutting half-ring 901 and the second cutting half-ring 902 are each of a wavy-line structure. In an embodiment, the first cutting half-ring 901 and the second cutting half-ring 902 with a wavy-line structure may be woven from metal wires.

Figure 10:
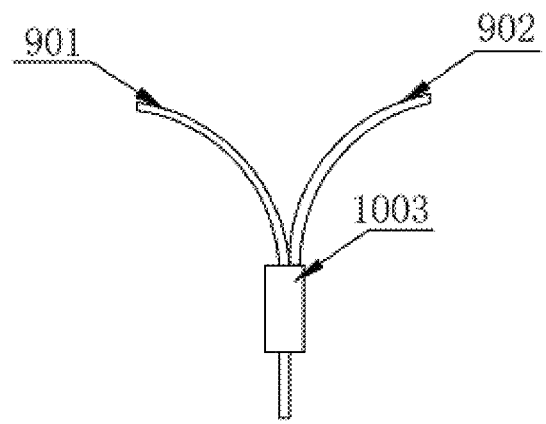
FIG. 10 is a side view of two cutting half-rings that are socketed to each other according to an embodiment of the present application.
Figure 11:
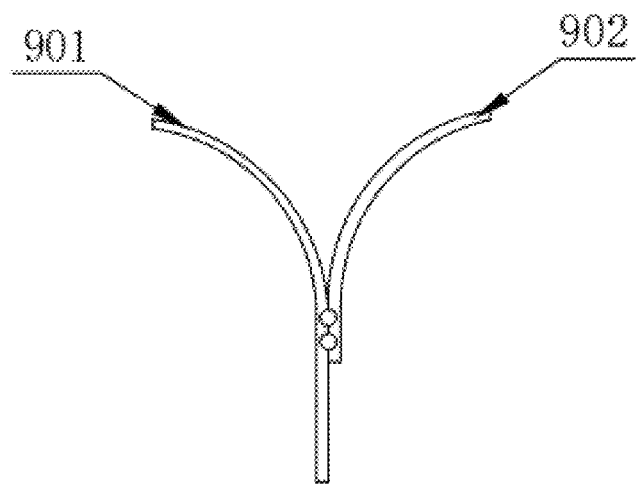
FIG. 11 is a side view of two cutting half-rings that are welded to each other according to an embodiment of the present application.

The first cutting half-ring 901 and the second cutting half-ring 902 may be sleeved on each other by using a metal connecting tube 1003, as shown in FIG. 10. As shown in FIG. 11, the first cutting half-ring 901 and the second cutting half-ring 902 may also be connected to each other by glue bonding or laser welding.

Figure 12:
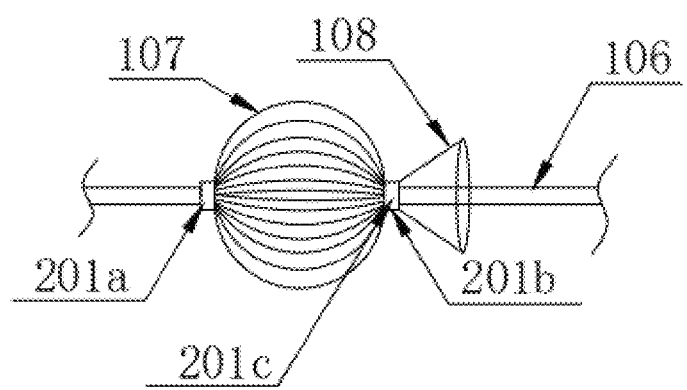
FIG. 12 is a structure view of a first cutting component and a second cutting component that are integrally connected to each other according to an embodiment of the present application.

In other embodiments, as shown in FIG. 12, the proximal third connecting ring 201c and the distal first connecting ring 201b are an integrated structure. The first cutting components 107 and the second cutting components 108 may be integrally cut from a metal tube, and the distal first connecting ring 201b is freely connected to the push tube 106 and moves as the diameter of the first cutting component 107 changes.

Figure 13:
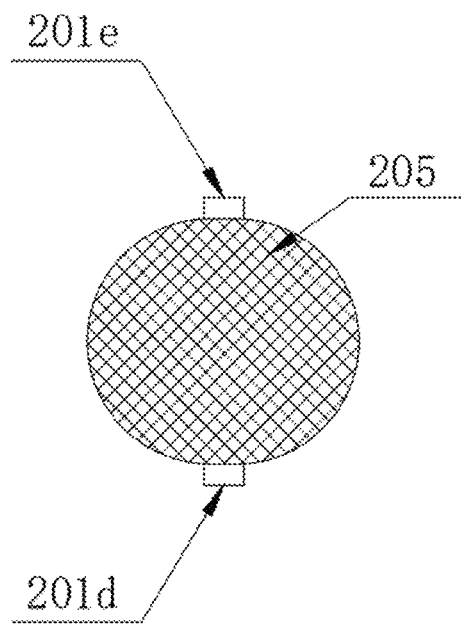
FIG. 13 is a first structure view of a collection device according to an embodiment of the present application.
Figure 14:
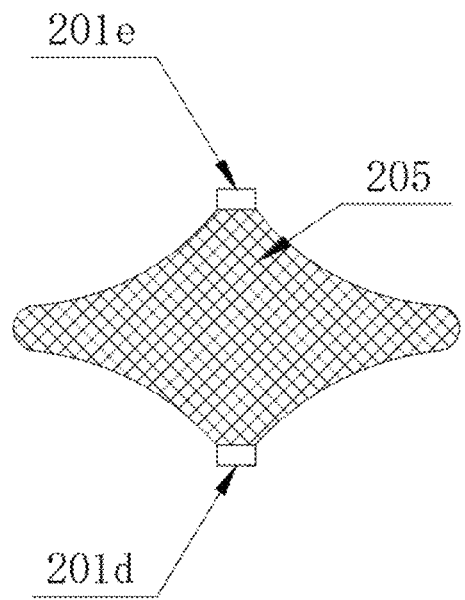
FIG. 14 is a second structure view of a collection device according to an embodiment of the present application.

As shown in FIGS. 1, 13 and 14, the collection device 109 includes a proximal fourth connecting ring 201d, a distal second connecting ring 201e and a first filter mesh 205 disposed between the proximal fourth connecting ring 201d and the distal second connecting ring 201e. The first filter mesh 205 can collect the thrombus 1802 without obstructing the blood flow. The collection device 109 may be of a mesh-shaped structure formed by cutting a medical metal tube or weaving medical metal wires. The mesh size of the first filter mesh 205 is small so that the detached embolus 2101 can be collected by the first filter mesh 205 and removed from the body via an aspiration catheter 104. The proximal fourth connecting ring 201d is fixedly disposed on the push tube 106, and the distal second connecting ring 201e is slidably disposed on the push tube 106. The proximal fourth connecting ring 201d is fixed to the push tube 106 by heat fusion, glue bonding or welding, and the distal second connecting ring 201e is freely connected to the push tube 106 and can slide back and forth relative to the tube wall of the push tube 106.

The material of the connecting rings in the embodiment herein may be a medical metal material such as medical stainless steel, nickel-titanium memory alloy, cobalt-base alloy, titanium alloy and magnesium alloy, may be a medical polymer material such as polyetheretherketone (PEEK), polytetrafluoroethylene (PTFE), polyethylene terephthalate (PET) and nylon, or may be a developing material such as platinum tungsten, platinum iridium, tantalum, platinum and gold to make two ends of the device developable, thereby helping to position the device in the conveyance and retraction process. The first filter mesh 205 has a small mesh size and can collect the detached embolus 2101 and remove the detached embolus 2101 from the body.

As shown in FIGS. 13 and 14, the first filter mesh 205 is of a spherical structure or a flat disc structure. The first filter mesh 205 with a flat disc structure has a stronger radial support force and a smaller mesh size and is made of a medical metal material. The medical metal material includes medical stainless steel, nickel-titanium memory alloy, cobalt-base alloy, titanium alloy and magnesium alloy. In other embodiments, the medical metal material may be a nickel-titanium memory alloy.

Figure 15:
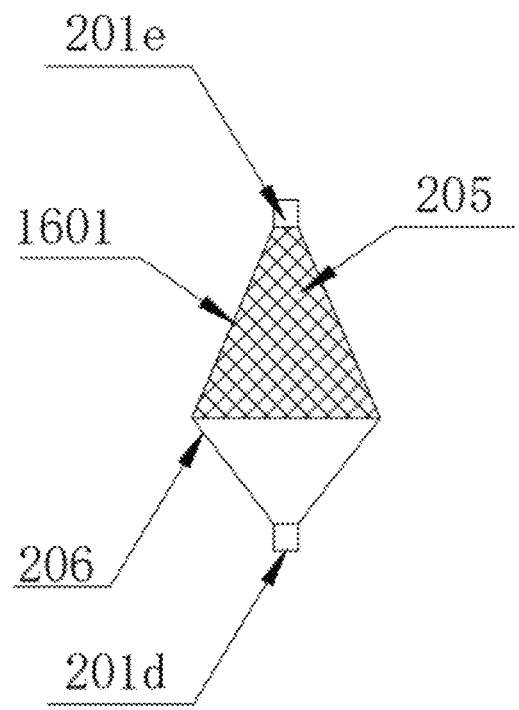
FIG. 15 is a third structure view of a collection device according to an embodiment of the present application.

In other embodiments, as shown in FIG. 15, the first filter mesh 205 is of a funnel-shaped structure, and the collection device 109 further includes a second connecting rod 206 and a skeleton 1601. After the thrombectomy device is released, the skeleton 1601 may support the first filter mesh 205 to form a funnel-shaped structure. The first end of the second connecting rod 206 is connected to the proximal fourth connecting ring 201d, and the second end of the second connecting rod 206 is connected to the wide mouth of the first filter mesh 205.

In an embodiment, the skeleton 1601 may be cut from a medical metal tube or woven from medical metal wires and provides radial support force for the collection device of the thrombus. The first filter mesh 205 is coated on the outer surface of the skeleton 1601 by heat fusion, bonding or welding. The first filter mesh 205 may be woven from medical wires or perforated from a medical film. The medical material may be medical stainless steel, nickel-titanium memory alloy, cobalt-base alloy, titanium alloy, magnesium alloy, expanded polytetrafluoroethylene (ePTFE), PET, polyurethane (PU), PEEK or polyethene (PE). The first filter mesh 205 has a thickness of about 10 μm to 2000 μm and a mesh diameter of about 10 μm to 1000 μm.

Figure 18:
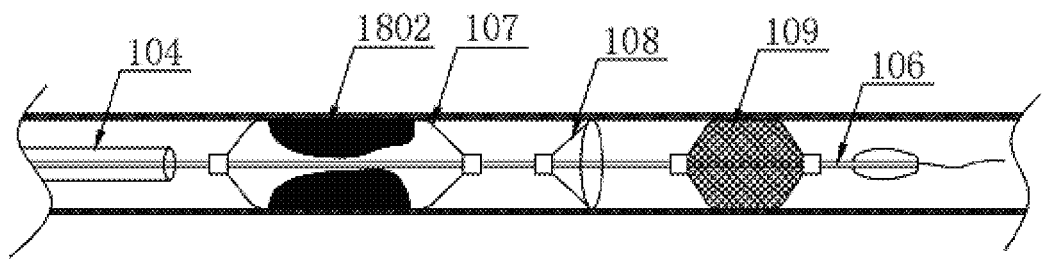
FIG. 18 is a view illustrating a step-cutting thrombectomy device entering a blood vessel and being released according to an embodiment of the present application.
Figure 19:
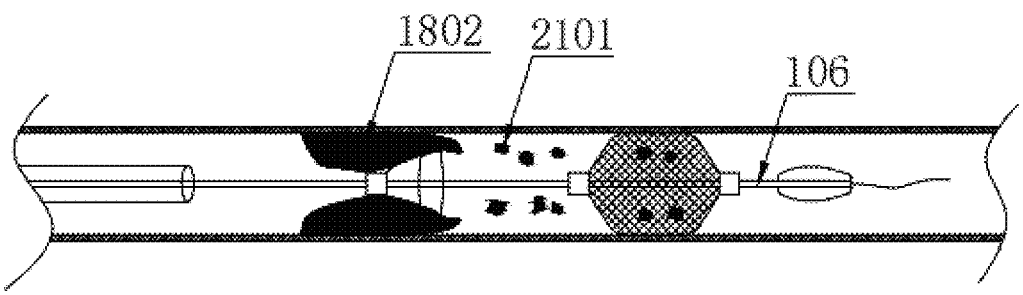
FIG. 19 is a view illustrating a second cutting component performing cutting in the circumferential direction according to an embodiment of the present application.
Figure 20:
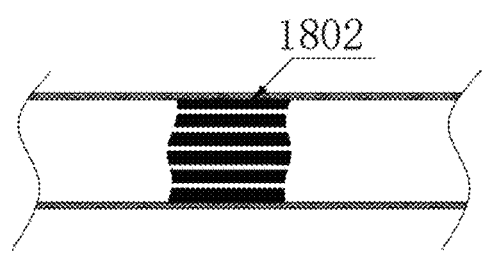
FIG. 20 is a view illustrating a thrombus cut by the first cutting component according to an embodiment of the present application.
Figure 21:
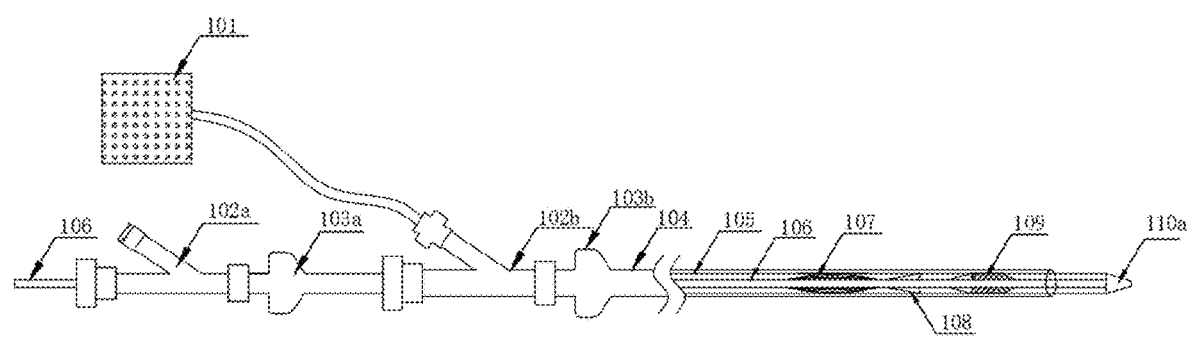
FIG. 21 is a structure view of a thrombectomy system according to an embodiment of the present application.

The embodiment herein further provides a thrombectomy system. As shown in FIG. 21, the thrombectomy system includes an aspiration pump 101, a hemostasis valve, a luer hub, an aspiration catheter 104, an outer tube 105 and the aforementioned step-cutting thrombectomy device. The aspiration pump 101 and the aspiration catheter 104 are connected via a second hemostasis valve 102b and a second luer hub 103b and are responsible for aspirating the crushed thrombus 1802 out of the body. The outer tube 105 is located within the aspiration catheter 104, and the proximal end of the outer tube 105 is connected to a first luer hub 103a and a first hemostasis valve 102a. The first cutting components 107, the second cutting components 108 and the collection device 109 are loaded within the outer tube 105 and are connected to the push tube 106 via a connection ring. The first cutting components 107, the second cutting components 108 and the collection device 109 are sequentially disposed from the proximal end to the distal end. The push tube 106 penetrates the entire thrombectomy system. The distal end of the push tube 106 is connected to a first tip guide cap 110a. A guidewire 1801 can pass through the inside of the push tube 106. During the surgery, the push tube 106 is secured, the first hemostasis valve 102a is retracted, and the device is released from the outer tube 105. At the end of the surgery, the aspiration catheter 104 is secured, the push tube 106 is retracted or the push tube 106 and the first hemostasis valve 102a are simultaneously retracted to pull back the device into the aspiration catheter 104 to remove the device from the body. The schematic views of the usage process of the thrombectomy system are shown in FIGS. 17 to 21. During the surgery, the guidewire 1801 passes through the lesion site, the aspiration catheter 104 is then delivered along the guidewire 1801 to the proximal end of the lesion site, and the thrombectomy device is delivered to a designated location along the guidewire 1801 and the aspiration catheter 104. As shown in FIG. 17, the location of the device is determined according to the developing component on the device to enable the first cutting components 107 overlap the position of the thrombus 1802. As shown in FIG. 18, the aspiration catheter 104 and the push tube 106 are secured. The outer tube 105 is retracted to the push tube 106 or removed from the body, and the components are released. After the components are released for a certain period of time in the blood vessel 1803, the diameter of the device gradually increases as the temperature rises. The first cutting components 107 produce a longitudinal cutting effect on the thrombus 1802 to cut the thrombus 1802 into small pieces, as shown in FIG. 20. The aspiration catheter 104 and the outer tube 105 are secured, and the push tube 106 is pulled back. During the pulling, the second cutting components 108 contact the thrombus 1802 and scrape the thrombus 1802 down from the wall of the blood vessel. The crushed embolus 2101 is trapped by the collection device 109 along with the blood flow, as shown in FIG. 19. The aspiration pump 101 is switched on while it continues pulling back the push tube 106 to aspirate the thrombus 1802 out of the body. If there is residual thrombus 1802 in the blood vessel 1803, the device may be re-released until the thrombus 1802 is completely removed. The aspiration catheter 104 is removed from the body upon completion of the surgery.

Embodiment Two

The embodiment herein provides a step-cutting thrombectomy device. In comparison with the device in embodiment one, the basic structure of the step-cutting thrombectomy device provided in the embodiment herein is the same as the structure of the device in embodiment one, except that the setting of the collection device 109 and the first longitudinal cutting member 202*a* herein is different. The same structure as that in embodiment one is not described in the embodiment herein.

Figure 4:
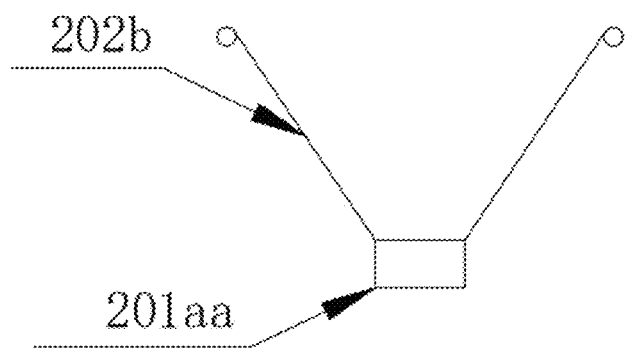
FIG. 4 is a third structure view of a first cutting component according to an embodiment of the present application.

In an embodiment, as shown in FIG. 4, the multiple first longitudinal cutting members 202*a* may also form a non-closed structure. The first cutting component 107 includes a proximal second connecting ring 201*aa* and second longitudinal cutting members 202*b*. Two second longitudinal cutting members 202*b* form a V-shaped structure. The proximal second connecting ring 201*aa* is fixedly disposed on the push tube 106. A first end of the second longitudinal cutting member 202*b* is fixedly connected to the proximal second connecting ring 201*aa*, and a second end of the second longitudinal cutting member 202*b* is provided with an annular bent portion. With an annular bent portion disposed at the end of the second longitudinal cutting member 202*b*, the end of the second longitudinal cutting member 202*b* is prevented from puncturing the blood vessel 1803, thereby improving surgical safety.

Figure 16:
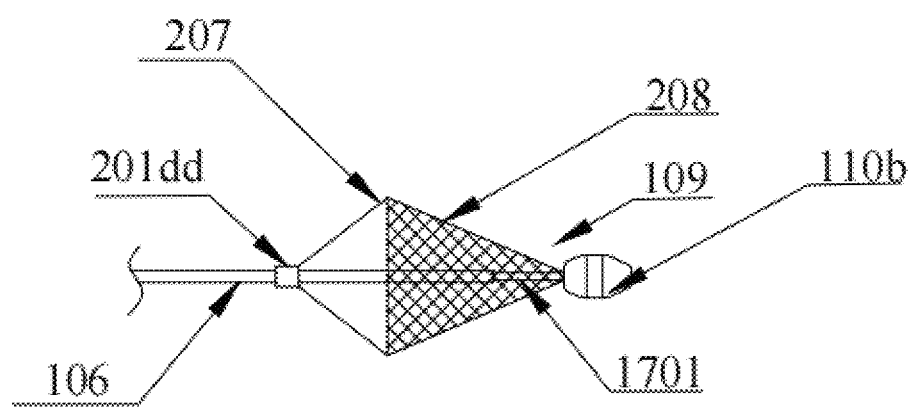
FIG. 16 is a fourth structure view of a collection device according to an embodiment of the present application.

In an embodiment, the collection device 109 may be connected in another manner, as shown in FIG. 16. The push tube 106 is provided with an inner tube 1701 passing through the push tube 106. The collection device 109 includes a proximal fifth connecting ring 201*dd*, a distal third connecting ring, a third connecting rod 207 and a second filter mesh 208, and the third connecting rod 207 and the second filter mesh 208 are sequentially disposed between the proximal fifth connecting ring 201*dd* and the distal third connecting ring. The second filter mesh 208 is a funnel-shaped structure. The proximal fifth connecting ring 201*dd* is fixedly disposed on the push tube 106. The distal third connecting ring is fixedly disposed on the inner tube 1701. The distal end of the inner tube 1701 is provided with a second tip guide cap 110*b*. The inner tube 1701 is a hollow structure to allow the guidewire 1801 to pass through. The proximal end of the inner tube 1701 is inserted into the push tube 106, and the inner tube 1701 can freely slide within the push tube 106. With the contraction and expansion of the collection device 109, the inner tube 1701 is extended or retracted towards the distal end or the proximal end. The inner tube 1701 may be a hypotube, a polymer tube or a braided tube.

What is claimed is:

1. A step-cutting thrombectomy device, comprising:
   a plurality of first cutting components elastically expandable in a radial direction, configured to cut a thrombus in a longitudinal direction of a blood vessel;
   a plurality of second cutting components elastically expandable in the radial direction, configured to cut the thrombus in a circumferential direction of the blood vessel, wherein a second cutting component among the plurality of second cutting components comprises a proximal third connecting ring, a first connecting rod and a transverse cutting ring, a first end of the first connecting rod is connected to the proximal third connecting ring, and a second end of the first connecting rod is connected to the transverse cutting ring, wherein the transverse cutting ring comprises a third cutting ring and a fourth cutting ring, an inner diameter of the third cutting ring is less than an inner diameter of the fourth cutting ring, and the third cutting ring and the fourth cutting ring are sequentially disposed on the first connecting rod at intervals in an axial direction of a push tube; and
   a collection device, configured to trap and collect a crushed thrombus;
   wherein the plurality of first cutting components, the plurality of second cutting components and the collection device are sequentially disposed on the push tube from a proximal end of the step-cutting thrombectomy device to a distal end of the step-cutting thrombectomy device.

2. The step-cutting thrombectomy device according to claim 1, wherein a first cutting component among the plurality of first cutting components comprises a proximal first connecting ring, a distal first connecting ring and at least one first longitudinal cutting member, a proximal end of the at least one first longitudinal cutting member is connected to the proximal first connecting ring, a distal end of the at least one first longitudinal cutting member is connected to the distal first connecting ring, the proximal first connecting ring is fixedly sleeved on the push tube, and the distal first connecting ring is slidably disposed on the push tube.

3. The step-cutting thrombectomy device according to claim 2, wherein a plurality of first longitudinal cutting members are disposed circumferentially at intervals and encircle outside the push tube.

4. The step-cutting thrombectomy device according to claim 1, wherein a first cutting component among the plurality of first cutting components comprises a proximal second connecting ring and a second longitudinal cutting member, the proximal second connecting ring is fixedly disposed on the push tube, a first end of the second longitudinal cutting member is fixedly connected to the proximal second connecting ring, and a second end of the second longitudinal cutting member is provided with an annular bent portion.

5. The step-cutting thrombectomy device according to claim 3, wherein the plurality of first cutting components are disposed on the push tube, and maximum outer diameters of the plurality of first cutting components gradually increase from the proximal end to the distal end.

6. The step-cutting thrombectomy device according to claim 1, wherein the proximal third connecting ring and the distal first connecting ring are an integrated structure.

7. The step-cutting thrombectomy device according to claim 1, wherein the proximal third connecting ring is fixedly disposed on the push tube.

8. The step-cutting thrombectomy device according to claim 1, wherein the plurality of second cutting components are disposed on the push tube, and maximum outer diameters of the plurality of second cutting components gradually increase from the proximal end to the distal end.

9. The step-cutting thrombectomy device according to claim 1, wherein the collection device comprises a proximal fourth connecting ring, a distal second connecting ring and a first filter mesh disposed between the proximal fourth connecting ring and the distal second connecting ring, the proximal fourth connecting ring is fixedly disposed on the push tube, and the distal second connecting ring is slidably disposed on the push tube.

10. The step-cutting thrombectomy device according to claim 9, wherein the first filter mesh is of a spherical structure or a flat disc structure.

11. The step-cutting thrombectomy device according to claim 9, wherein the first filter mesh is of a funnel-shaped structure, the collection device further comprises a second connecting rod, a first end of the second connecting rod is connected to the proximal fourth connecting ring, and a second end of the second connecting rod is connected to a wide mouth of the first filter mesh.

12. The step-cutting thrombectomy device according to claim 1, wherein an inner tube passing through the push tube is disposed in the push tube, and the collection device comprises a proximal fifth connecting ring, a distal third connecting ring, a third connecting rod and a second filter mesh, wherein the third connecting rod and the second filter mesh are sequentially disposed between the proximal fifth connecting ring and the distal third connecting ring, the second filter mesh is of a funnel-shaped structure, the proximal fifth connecting ring is fixedly disposed on the push tube, the distal third connecting ring is fixedly disposed on the inner tube, and a distal end of the inner tube is provided with a second tip guide cap.

13. A thrombectomy system, comprising an aspiration pump, a hemostasis valve, a luer hub, an aspiration catheter, an outer tube and a step-cutting thrombectomy device, wherein the step-cutting thrombectomy device comprises:
a plurality of first cutting components elastically expandable in a radial direction, configured to cut a thrombus in a longitudinal direction of a blood vessel;
a plurality of second cutting components elastically expandable in the radial direction, configured to cut the thrombus in a circumferential direction of the blood vessel, wherein a second cutting component among the plurality of second cutting components comprises a proximal third connecting ring, a first connecting rod and a transverse cutting ring, a first end of the first connecting rod is connected to the proximal third connecting ring, and a second end of the first connecting rod is connected to the transverse cutting ring, wherein the transverse cutting ring comprises a third cutting ring and a fourth cutting ring, an inner diameter of the third cutting ring is less than an inner diameter of the fourth cutting ring, and the third cutting ring and the fourth cutting ring are sequentially disposed on the first connecting rod at intervals in an axial direction of a push tube; and
a collection device, configured to trap and collect a crushed thrombus, wherein the plurality of first cutting components, the plurality of second cutting components and the collection device are sequentially disposed on the push tube from a proximal end of the step-cutting thrombectomy device to a distal end of the step-cutting thrombectomy device.

14. The thrombectomy system according to claim 13, wherein a first cutting component among the plurality of first cutting components comprises a proximal first connecting ring, a distal first connecting ring and at least one first longitudinal cutting member, a proximal end of the at least one first longitudinal cutting member is connected to the proximal first connecting ring, a distal end of the at least one first longitudinal cutting member is connected to the distal first connecting ring, the proximal first connecting ring is fixedly sleeved on the push tube, and the distal first connecting ring is slidably disposed on the push tube.

15. The thrombectomy system according to claim 14, wherein a plurality of first longitudinal cutting members are disposed circumferentially at intervals and encircle outside the push tube.

16. The thrombectomy system according to claim 13, wherein a first cutting component among the plurality of first cutting components comprises a proximal second connecting ring and a second longitudinal cutting member, the proximal second connecting ring is fixedly disposed on the push tube, a first end of the second longitudinal cutting member is fixedly connected to the proximal second connecting ring, and a second end of the second longitudinal cutting member is provided with an annular bent portion.

17. The thrombectomy system according to claim 16, wherein the plurality of first cutting components are disposed on the push tube, and maximum outer diameters of the plurality of first cutting components gradually increase from the proximal end to the distal end.

18. The thrombectomy system according to claim 13, wherein the proximal third connecting ring and the distal first connecting ring are an integrated structure.

19. The thrombectomy system according to claim 13, wherein the proximal third connecting ring is fixedly disposed on the push tube.

20. The thrombectomy system according to claim 13, wherein the plurality of second cutting components are disposed on the push tube, and maximum outer diameters of the plurality of second cutting components gradually increase from the proximal end to the distal end.

* * * * *